United States Patent
Rom

(10) Patent No.: US 9,089,709 B2
(45) Date of Patent: Jul. 28, 2015

(54) SYSTEM AND METHOD FOR THE VISUALIZATION AND OPTIMIZATION OF CARDIAC RESYNCHRONIZATION THERAPY

(75) Inventor: Rami Rom, Zichron Yaakov (IL)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 13/282,720

(22) Filed: Oct. 27, 2011

(65) Prior Publication Data

US 2012/0071943 A1    Mar. 22, 2012

Related U.S. Application Data

(63) Continuation-in-part of application No. 11/721,449, filed as application No. PCT/IL2005/001288 on Dec. 1, 2005, now abandoned.

(30) Foreign Application Priority Data

Dec. 12, 2004    (IL) .......................................... 165729

(51) Int. Cl.
*A61N 1/368*    (2006.01)
*A61N 1/362*    (2006.01)
*A61N 1/372*    (2006.01)
*G06F 19/00*    (2011.01)

(52) U.S. Cl.
CPC ............ *A61N 1/3627* (2013.01); *A61N 1/3682* (2013.01); *A61N 1/3684* (2013.01); *A61N 1/37247* (2013.01); *G06F 19/3418* (2013.01)

(58) Field of Classification Search
CPC .............................. A61N 1/368; A61N 1/3682
USPC .................................................. 607/25, 27, 30
See application file for complete search history.

(56) References Cited

U.S. PATENT DOCUMENTS

| | | | |
|---|---|---|---|
| 6,223,079 B1 | 4/2001 | Bakels et al. | |
| 6,522,923 B1 | 2/2003 | Turcott | |
| 6,792,310 B1 * | 9/2004 | Turcott et al. | 607/27 |
| 7,130,689 B1 * | 10/2006 | Turcott | 607/27 |
| 2003/0013977 A1 * | 1/2003 | Daum | 600/508 |
| 2004/0030356 A1 | 2/2004 | Osypka | |
| 2004/0158293 A1 | 8/2004 | Yonce | |
| 2004/0181260 A1 * | 9/2004 | Anderson et al. | 607/17 |
| 2006/0235477 A1 | 10/2006 | Rom | |
| 2007/0129764 A1 * | 6/2007 | Burnes | 607/18 |
| 2009/0030471 A1 * | 1/2009 | Rousso et al. | 607/27 |

* cited by examiner

*Primary Examiner* — George Evanisko
(74) *Attorney, Agent, or Firm* — Simon Kahn; Chanoch Kahn

(57) ABSTRACT

A system and method for optimizing cardiac resynchronization therapy and visualizing cardiac pacing intervals. The system comprises at least one hemodynamic sensor; at least one electrode; a learning module; a micro controller; and at least one graphical interface for showing at least one of a PRV vs. PLV diagram and a responder curve.

6 Claims, 5 Drawing Sheets

SYSTEM AND METHOD FOR THE VISUALIZATION AND OPTIMIZATION OF CARDIAC RESYNCHRONIZATION THERAPY

CROSS-REFERENCE TO RELATED PATENT APPLICATIONS

This application is a continuation-in-part of prior U.S. patent application Ser. No. 11/721,449, filed Jun. 12, 2007 now abandoned, which was a national stage entry of International Patent Application No. PCT/IL2005/001288, titled "Optimizing and Monitoring Adaptive Cardiac Resynchronization Therapy Devices" and filed on Dec. 1, 2005, and which claims priority from Israel Patent Application No. IL 165729, titled "Method for Optimizing Cardiac Resynchronization Therapy Devices", filed on Dec. 12, 2004, the entire contents of all of which applications are incorporated herein by reference.

FIELD OF THE INVENTION

The present invention relates to cardiac pacemaker and defibrillator devices and more specifically to a system and method for optimizing cardiac resynchronization therapy.

BACKGROUND OF THE INVENTION

Cardiac Resynchronization Therapy (CRT), delivered by implanted pacemakers and intracardiac cardioverter defibrillators, is currently an established therapy for patients with congestive systolic heart failure and intraventricular electrical or mechanical conduction delays, as described, for example, in Clinical Cardiac Pacing and Defibrillation, $2^{nd}$ edition, Ellenbogen, Kay, Wilkoff, 2000. Cardiac output depends strongly on the left heart contraction being in synchrony with the right atrium and ventricle of the heart (see U.S. Pat. No. 6,223,079). Congestive heart failure is defined generally as the inability of the heart to deliver enough blood to meet the metabolic demand. Often, congestive heart failure is caused by one or more electrical conduction defects. The overall result is a reduced blood stroke volume from the left side of the heart. For congestive heart failure patients, CRT is an effective treatment employing a permanent pacemaker with electrodes in three chambers that re-synchronize the pacing of the atrium and the left and right ventricles ["Device Therapy for Congestive Heart Failure", K. Ellenbogen et al, Elsevier Inc. (USA), 2004]. The resynchronization task demands exact pacing management of the heart chambers such that the overall stroke volume is maximized for a given heart rate. Optimal timing of activation of the atrium and the right and left ventricles is one of the key factors influencing cardiac output, where the main intent is to cause the left ventricle to contract in synchrony with the right ventricle. The timing parameters that are programmed in a CRT device that determines the pacing intervals are atrioventricular (AV) delay and interventricular (VV) interval. AV delay is the delay in cardiac pulse moving from the atria to the right ventricle; and VV interval is the time interval between right and left ventricle stimulations. The VV interval can be either negative or positive. When the VV interval is negative, the left ventricle is stimulated before the right ventricle; and when the VV interval is positive, the left ventricle is stimulated after the right ventricle. When monitoring cardiac pacing, two major parameters are registered—PRV and PLV. PRV is the right ventricle pacing interval, or in other words, the time interval between sensed atrial stimulation and sensed right ventricle stimulation. Thus PRV is equal to AV delay. PLV is the left ventricle pacing interval, or the time interval between sensed atrial stimulation and sensed left ventricle stimulation. Hence, PLV equals AV delay plus VV interval.

The re-synchronization task is patient and activity dependent, in that for each patient the best combination of pacing time intervals that restores synchrony is changed during normal daily activities of the patient.

The reasons that the currently available CRT devices cannot achieve optimal delivery of CRT are as follows:

1. Programming and troubleshooting the CRT device—currently, optimizing the CRT device using echocardiography is expensive, time consuming and operator dependent. The clinician is required to optimize both the AV delay and VV interval in order to achieve resynchronization of heart chamber contractions.

2. Consistent Delivery of CRT—There are several reasons why CRT is not delivered consistently, and at times not delivered at all for hours. Two reasons for this are failure to optimize the AV delay and the low value of the programmed maximal tracking rate.

3. Follow ups—The clinician must perform the complex task of optimization and programming of the CRT device, first during implantation and then at each follow-up.

4. CRT non-responders—a significant number of patients, typically about 30%, do not respond to CRT after implantation. The development of good markers that will enable identification of responders to CRT is a major issue due to the complexity of the instrumentation, the need for device implantation, and the medical costs associated with the treatment (David A. Kaas, "Ventricular Resyncronization: Patophysiology and Identification of Responders", Reviews in Cardiovascular Medicine, Vol. 4, Suppl. 2, 2003).

In this respect, Hayes et al. In "Resynchronization and Defibrillation for Heart Failure, A Practical Approach", Blackwell Publishing, 2004, suggest that optimal programming of the CRT device may turn "non responders" into "responders" and "responders" into better "responders".

SUMMARY OF THE INVENTION

Accordingly, it is an object of particular embodiments of the present invention to provide a system and method for cardiac re-synchronization therapy having online adaptive capabilities in order to adjust to the hemodynamic performance.

The present invention relates to a system and a method for optimizing CRT device activity which visualizes data obtained by dynamic active diagnostics. This enables a clinician to determine the CRT device's optimal AV delay and VV interval parameters, according to data obtained during an electrophysiology study and also to identify patients who do respond to CRT.

According to one aspect, the present invention provides a system for optimizing cardiac resynchronization therapy and visualizing cardiac pacing intervals, the system comprising: at least one hemodynamic sensor for monitoring hemodynamic performance of the heart, comprising at least a stroke volume value; at least one electrode for sensing at least one event selected from the group consisting of a right atrium event, a right ventricle event and left ventricle electrogram event; and in turn for pacing at least one of the right atrium, right ventricle or left ventricle; a learning module that learns to adapt at least one of atrio-ventricular (AV) delay intraventricular (VV) interval, as sensed by the at least one electrode, relatively to the hemodynamic performance of the heart as reflected in the stroke volume sensed by the at least one hemodynamic sensor; a micro controller for controlling the learning module; at least one pulse generator controlled by the micro controller, for stimulating the heart with optimized atrio-ventricular (AV) delay intra-ventricular (VV) interval parameters; and at least one graphical interface for showing at least one of a PRV vs. PLV diagram and a responder curve.

According to another aspect, the present invention provides a method of visualizing optimized cardiac pacing intervals, generated by a system comprising at least one hemodynamic sensor, at least one sensing electrode and at least one pacing electrode, a learning module, a micro controller, a pulse generator and at least one graphical interface, the method comprising the steps of providing at least a PRV vs. PLV diagram that visualizes a self convergence to optimal values of paced atrioventricular delay and interventricular interval character to an optimized hemodynamic performance; determining the optimal atrioventricular delay at all heart rates according to the PRV vs. PLV diagram; and determining the optimal interventricular interval at all heart rates according to the PRV vs. PLV diagram.

According to yet another aspect, the present invention provides a system for a remote monitoring of an adaptive cardiac resynchronization therapy device performance, for monitoring the patient's hemodynamic response to pacing with dynamically optimized atrioventricular delay and interventricular interval parameters and pacing consistency beat after beat in both rest and exercise, comprising: a graphical interface of a remote computer; at least one responder curve presenting the internally calculated stroke volume obtained by an implanted hemodynamic sensor, the responder curve, being displayed on the graphical interface; and a means for communicating the internally calculated stroke volume to the remote computer.

DETAILED DESCRIPTION OF THE INVENTION

Figure 1:
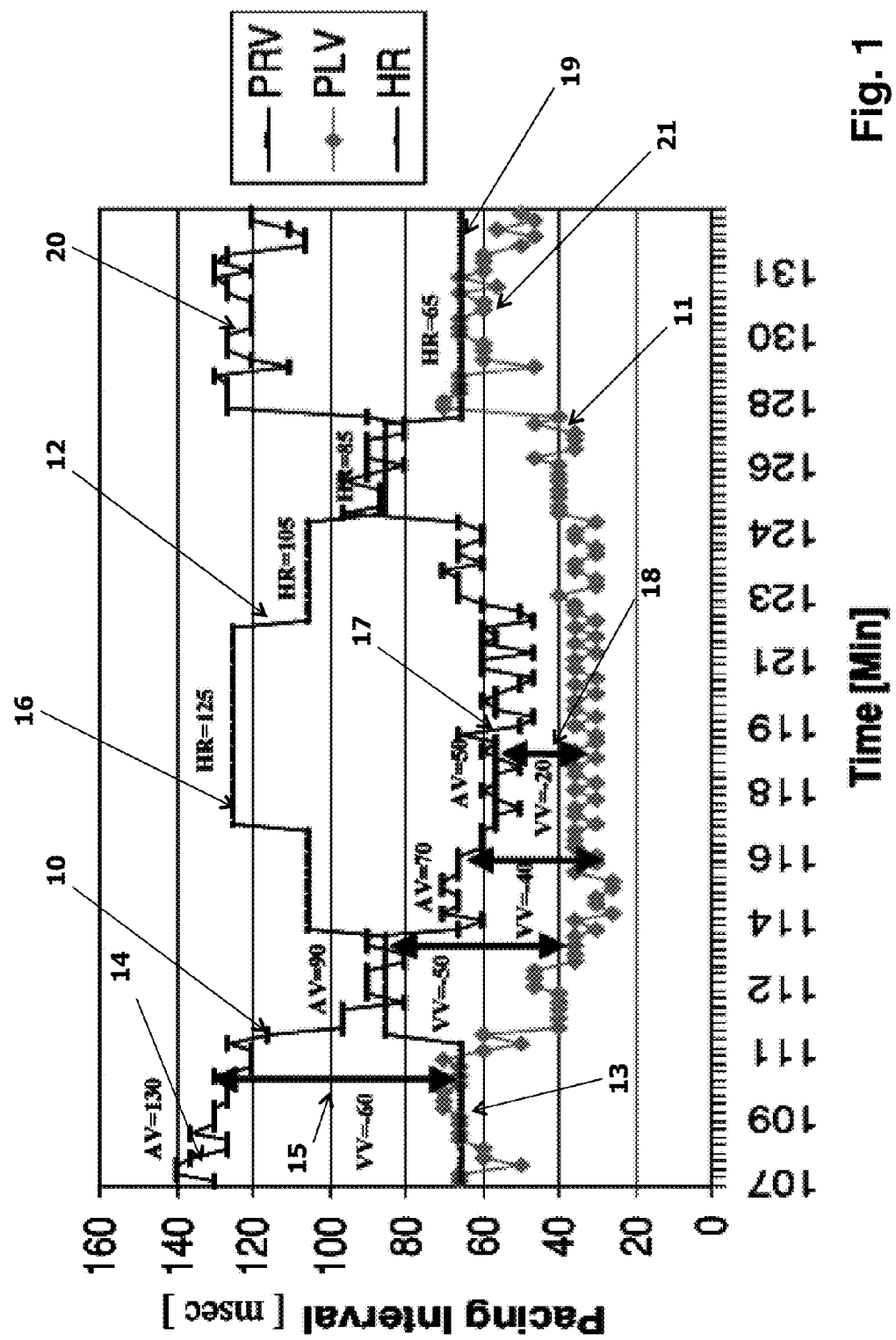
FIG. 1 is a plot showing dynamic optimization of an AV delay and VV interval parameters in response to changes in heartbeat rate, performed by an adaptive CRT device simulation setup.

A system for optimizing cardiac resynchronization therapy devices, to which the present invention is related, is aimed at optimizing the hemodynamic performance of the heart, namely the volumetric flow of blood produced by the heart at each heartbeat (i.e. stroke volume), according to a given physiological condition or state of the heart, as reflected in signals collected by a hemodynamic sensor. This goal is achieved by processing cardiac electrical signals and hemodynamic parameters collected by a hemodynamic sensor and delivering optimized CRT pacing to the heart, by dynamically changing the AV delay and VV interval pacing parameters according to the hemodynamic performance as sensed by hemodynamic sensors. A detailed technical description of an adaptive CRT device is given in U.S. Pat. No. 7,657,313, the content of which is incorporated herein by reference. Briefly, an adaptive CRT device comprises a microcontroller; a pulse generator module; and a learning module, for example, a spiking neural network co-processor. The adaptive CRT device further includes cardiac electrodes and at least one hemodynamic sensor. The spiking neural network co-processor is a learning module that processes cardiac electrograms as collected by the cardiac electrodes, placed in or on the heart and hemodynamic performance as sensed by the hemodynamic sensor. During the processing of the cardiac electrograms and the hemodynamic performance, the learning module calculates, heartbeat-to-heartbeat, a prediction of the optimal AV delay and VV interval parameters. The microcontroller is the master of the electrical system and manages the pulse generator module and acts also as a teacher that trains the neural network processor online.

Rom, Erel, Glickson, Rosenblum, Ginosar and Hayes, "Adaptive cardiac resynchronization therapy device: a simulation report, PACE—Pacing and Clinical Electrophysiology, Vol. 26, pp 1168-1173 (referred to herein after as Rom et al, 2005), and Rom and DalMolin, "Optimal cardiac pacing with Q learning, in "Advances in Reinforcement Learning", Mellouk, A., ed., InTech, 2011, pp. 451-470, describe an adaptive CRT device simulation setup, comprising a heart simulator linked to an adaptive CRT device. The heart simulator responds to pacing, delivered from the adaptive CRT device, according to a physiological state pre-programmed therein, and transmits right atrial, right ventricular, and left ventricular electro-grams, as well as hemodynamic signals in the form of right and left ventricular impedance outputs representing stroke volumes, to the adaptive CRT device. The adaptive CRT device, in turn, dynamically changes the AV delay and VV interval parameters, according to the hemodynamic input, and transmits these pacing parameters to the heart simulator. The data shown in the Figures described below are based on experiments conducted with an adaptive CRT device simulation setup, and are considered as examples of real data that are obtained with patients treated with an adaptive CRT system according to the present invention.

In one embodiment the present invention provides a combined electrophysiological testing system, which enables pacing of the ventricles and sensing of both intracardiac electro-grams and hemodynamic performance in real time for optimization of CRT devices during or after their implantation.

In another embodiment the present invention, a system is provided that employs an implanted biventricular pacemaker or a non-adaptive CRT device, in which both AV delay and VV interval are device parameters, programmed initially by a programmer into the device. These parameters (AV delay and VV interval) are then changed dynamically by either an adaptive CRT device or an adaptive CRT-D device (CRT device combined with a defibrillator), and the hemodynamic performance (such as stroke volume) is monitored by an implanted sensor or by a non-invasive monitoring appliance and used as a feedback to the learning module of an external adaptive CRT programmer.

In yet another embodiment, the present invention provides a system and method for optimizing the AV delay and VV interval parameters at a given heart rate, by dynamically diagnosing and visualizing the preferred parameters of either non-adaptive CRT (and CRT-D) devices or adaptive CRT (and CRT-D) devices, as described herein below. For a given heart rate, for example at rest heart rates and at gradually higher heart rates, the pacing interval of the right and left ventricles are changed dynamically by a learning module according to a feedback received from a hemodynamic sensor.

Figure 5:
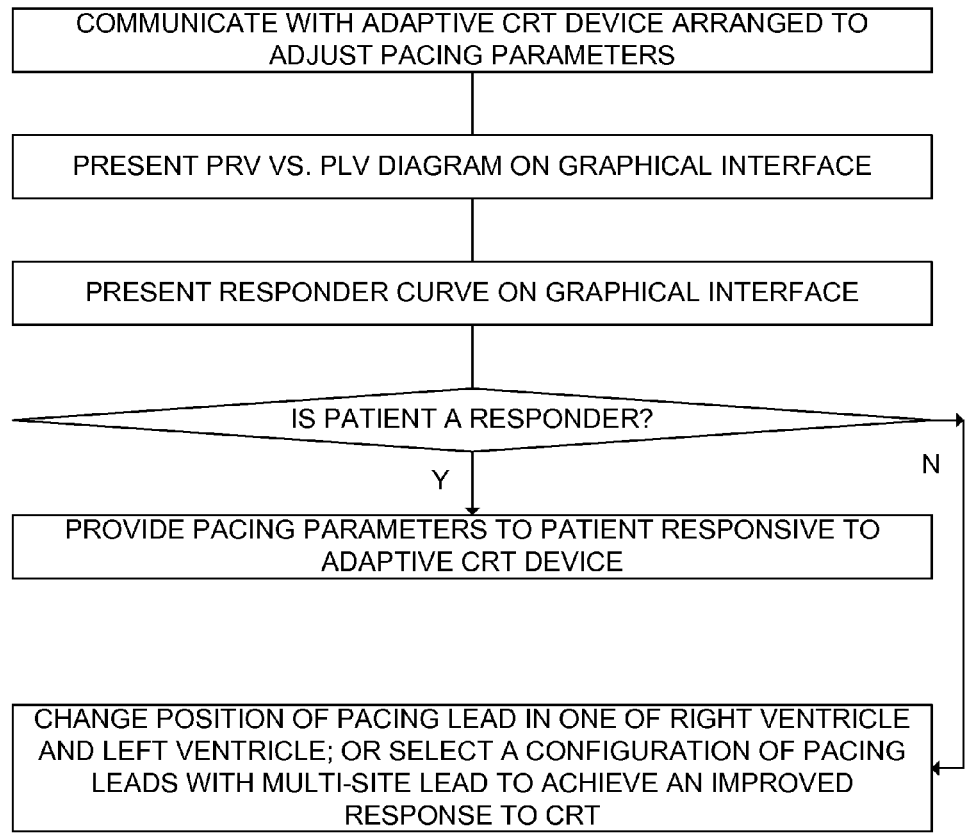
FIG. 5 is a flow chart of a method according to the present invention.

FIG. 1 shows an example of a dynamic optimization of the AV delay and VV interval parameters in response to changes in heartbeat rate, performed by the adaptive CRT device simulation setup mentioned above. This figure was published earlier as FIG. 5 in Rom et al, 2005, and is given here for the purpose of illustration and clarification of the process of dynamic optimization of the AV delay and VV interval parameters in response to changes in heartbeat rate. This Figure is a plot of PRV and PLV, measured during changes in heart rate, as a function of time.

PRV is defined as the time period that lapses from the time-point when a right atrial electrogram event is detected, indicating the commencement of the cardiac contraction cycle, to the time-point of the contraction of the right ventricle, namely the AV delay. PLV is defined as the time period that lapses from the time-point when a right atrial electrogram event is detected, indicating the commencement of the cardiac contraction cycle, to the time-point of the contraction of the left ventricle, namely the value of the AV delay plus the value of the VV interval.

The AV delay (data points 10), shown in FIG. 1, is equal to PRV (AV delay=PRV), and the VV interval is the difference between PLV (graph 11) and PRV (curve 10) (VV interval=PLV−PRV). In FIG. 1 changes in the heart rate (curves 12) as well as the changes in AV delay (curve 10) and VV interval, where the later were optimized by an adaptive CRT device, are shown as the function of time. At a heart rate of 65 beats per minute (indicated by reference numeral 13), as it was determined by the heart simulator, the optimized AV delay was 130 milliseconds (indicated by reference numeral 14), and the VV interval was −60 msec (indicated by reference numeral 15). When the heart rate was increased gradually to 125 beats per minute (indicated by reference numeral 16) the AV delay was reduced gradually, in parallel, to 50 msec (indicated by reference numeral 17), and the VV interval was reduced to −20 msec (indicated by reference numeral 18). When the heart rate was decreased back to 65 beats per minute (indicated by reference numeral 19) the AV delay increased to 125 msec (indicated by reference numeral 20), and the VV interval increased to −60 msec (indicated by reference numeral 21). Rom et al, 2005, indicate that this dynamic optimization of the AV delay and VV interval in response to changes in heart rate is based on changes in hemodynamic parameters, such as stroke volume, as carried out by the adaptive CRT device.

Figure 2:
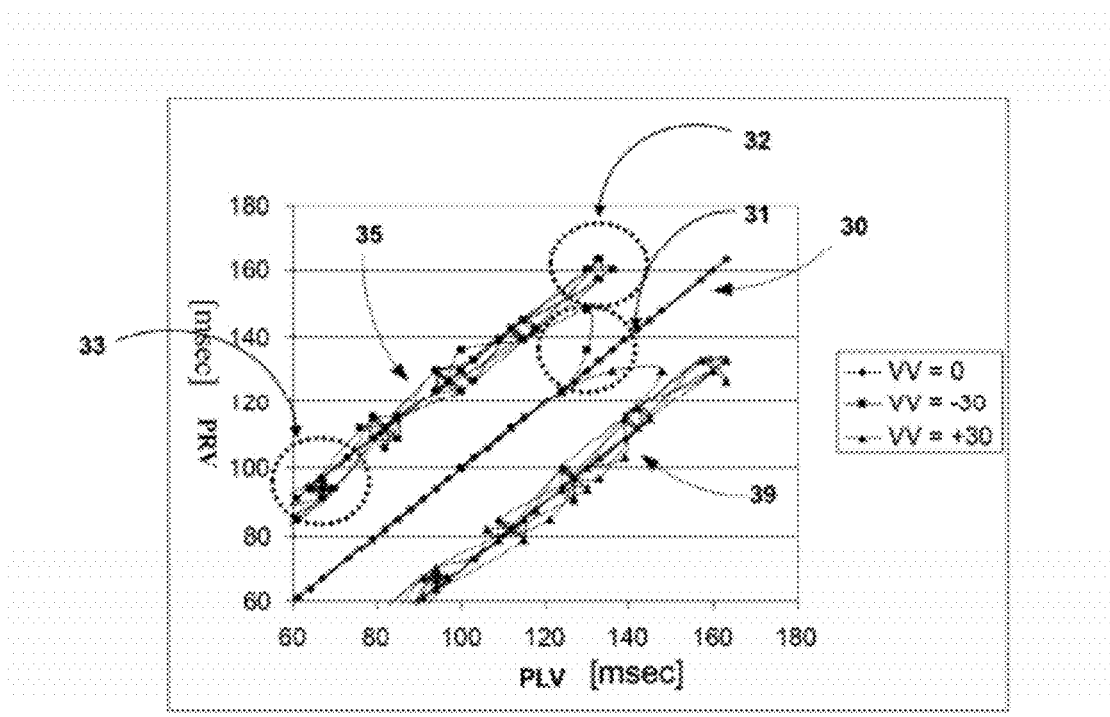
FIG. 2 is a plot showing PRV vs. PLV data obtained during optimization of AV delay and VV interval for achieving maximal stroke volume for three simulated Patients I, II and III.

FIG. 2 is a diagram of PLV versus PRV, showing the pacing parameters (namely AV delay and VV interval) that yielded the highest stroke volume, at a given heart rate as recorded during a simulation as described above (FIG. 1). Each point in the diagram is a combination of PRV and PLV values as advised by the learning module, when the vertical axis shows the PRV values in msec, and the horizontal axis shows the PLV values in msec.

The PRV vs. PLV diagram of FIG. 2, shows the response of a patient to applied adaptive CRT, affected continuously, and includes the information needed in order to optimally program non-adaptive CRT devices or adaptive CRT devices. The simulated results of three cases are shown in FIG. 2. Data points 30 are PRV and PLV values obtained from simulated Patient I that received simultaneous biventricular pacing, in which the highest stroke volume is obtained with a simultaneous pacing of both ventricles, i.e. VV interval=0. Therefore, for this patient, PRV=PLV, as can be seen in data points 30. Data points 35 are PRV and PLV values obtained from simulated Patient II. Pacing of the heart of simulated Patient II started with a VV interval=0. However, as can be seen in area 31 of data points 30, the VV interval changed to −30 msec as a result of the optimization process of the pacing parameters, carried out by the learning module, in response to the hemodynamic performance of Patient II, i.e. the stroke volume. In other words, Patient II achieved a maximal stroke volume when the left ventricle was paced 30 msec before the right ventricle (VV interval=−30 msec). This caused a shift upwards of the PRV vs. PLV diagram (data points 35), compared to the diagram of Patient I (data points 30). Another phenomenon that can be seen in the PRV vs. PLV diagram is the convergence of the PRV and PLV values in response to a change in heart rate. At a low heart rate, PRV and PLV converged accordingly towards higher values, as can be seen for instance in area 32 of data points 35. However, when the heart rate of simulated Patient II was increased, the PRV and PLV converged towards lower values, for instance area 33 of data points 35.

Data points 39 are PRV and PLV values obtained from simulated Patient III. The pacing of this patient started also with VV interval=0, however the pacing was adapted to a VV interval of +30 msec, or in other words, maximal stroke volume of Patient III was achieved when the left ventricle was paced 30 msec after the right ventricle. This caused a shift downwards of the PRV vs. PLV diagram (data points 39), compared to the diagram of Patient I (data points 30).

Figure 3:
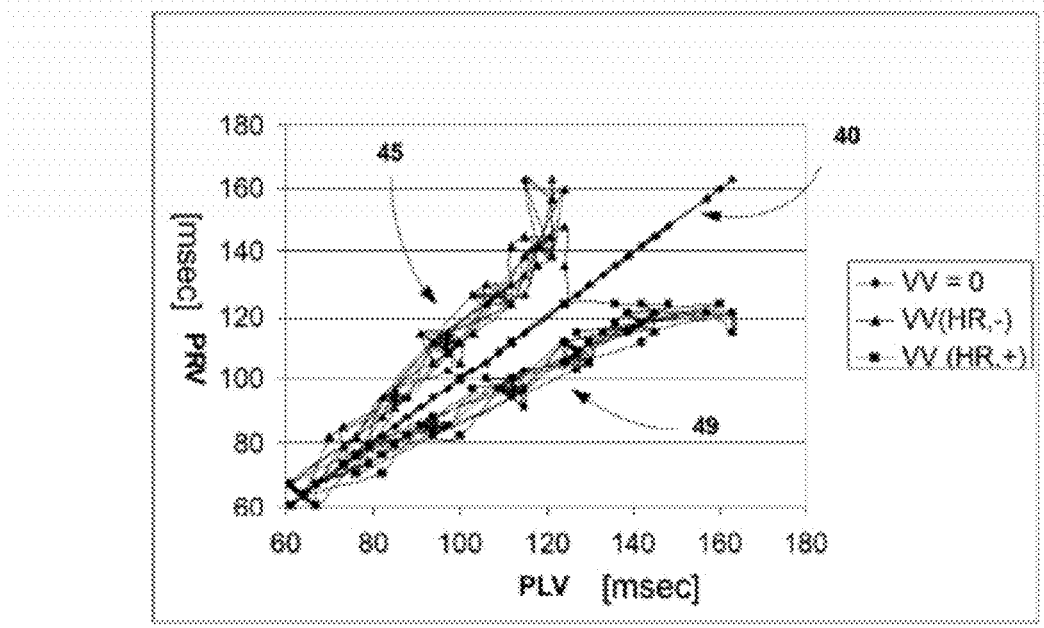
FIG. 3 is a plot showing PRV vs. PLV data obtained during optimization of AV delay and VV interval for achieving maximal stroke volume for three simulated Patients IV, V and VI.

FIG. 3 shows the results from three simulated cases. In these simulated cases, the left ventricle of the heart simulator evoked a simulated response delay time that depended on the heart rate. At a heart rate in rest, the left ventricle evoked response delay time is maximal (+/−40 msec) and as the heart rate increased, the left ventricle evoked response delay time decreased. On the PRV vs. PLV diagram this dependency is seen clearly. Data points 40 are PRV and PLV values obtained from simulated case IV that received simultaneous biventricular pacing like Patient I, represented by data points 30 in FIG. 2. Data points 45 in FIG. 3, are PRV and PLV values obtained from case V—a simulated patient that needs left ventricle pacing earlier than right ventricle pacing and a variable VV interval. Data points 49 are PRV and PLV values obtained from simulated Patient VI, who achieved optimal hemodynamic performance when the left ventricle pacing lagged after the right ventricle with a variable VV interval.

Consequent to the above, the PRV vs. PLV diagram can be used as a dynamic diagnostic tool that presents graphically the characteristics of a response of a heart failure patient to CRT. It can be used to study the VV interval sign and magnitude, as well as the heart rate dependence, all of which are presented online in one diagram during a continuous electrophysiology study.

In U.S. Pat. No. 7,657,313, an implanted or external adaptive CRT device is described, in which the AV delays and the VV intervals are changed dynamically by the implanted device that hence performs dynamic optimization of these important pacing parameters (the AV delay and VV interval). The change is affected in correspondence with the data derived from an invasive or non-invasive hemodynamic sensor in a closed loop using a neural network-learning module. With the adaptive CRT device, the PRV vs. PLV diagram of maximal stroke volume presented here is obtained automatically by the operating device and according to embodiments of the present invention the PRV vs. PLV diagram can be presented on a graphical interface, which is typically an electronic display device of an external programmer or on the external adaptive CRT device display screen.

Figure 6:
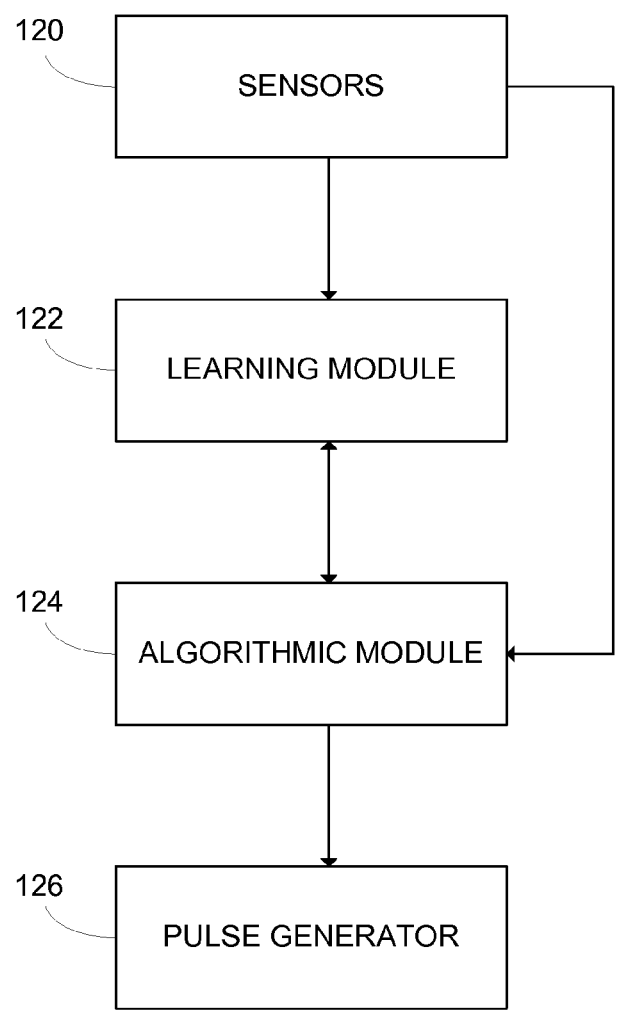
FIG. 6 is a schematic general description of an adaptive CRT system of the present invention.

In FIG. 6, sensors 120 feed physiological information of the patient into a learning module which is typically a neural network module 122 and to the algorithmic module 124. Algorithmic module 124 receives processed data form the neural network module 122 and controls the adaptations schemes of the neural network module 122. Pulse generator 126 issues impulses at the time and places as controlled only by algorithmic module 124.

In a preferred embodiment the system as described above forms a unitary block implanted in the patient's heart, a cardiac pacemaker or defibrillator, with sensors 120 positioned at critical sites, and pulsing electrodes applied at strategic sites in or about the heart. In other embodiments, only the pacing module is implanted, whereas the neural network module 122 is not implanted in the patient's body; but is communicable through a communications link. Accordingly the neural network module 122 receives through a typically wireless link, information regarding hemodynamic condition of the patient and the electrical behavior of the heart.

The present invention also provides a combined electrophysiological testing system and method for optimizing lead positioning during the implantation procedure of CRT devices. More particularly, the system provided by the present invention enables pacing of the ventricles and sensing both intracardiac electrograms and hemodynamic performance in real time during CRT device implantation, thus enabling optimization of the performance of the CRT devices during implantation. This is achieved by identifying whether the patient responds to CRT or not.

The adaptive CRT device described in U.S. Pat. No. 7,657,313 and the system for optimizing cardiac resynchronization therapy by visualizing cardiac pacing intervals of the present invention allow the identification of a responder to CRT during several minutes of continuous biventricular pacing in an electrophysiology test during the implantation process of the adaptive CRT device, or when programming an implanted adaptive CRT device.

Figure 4:
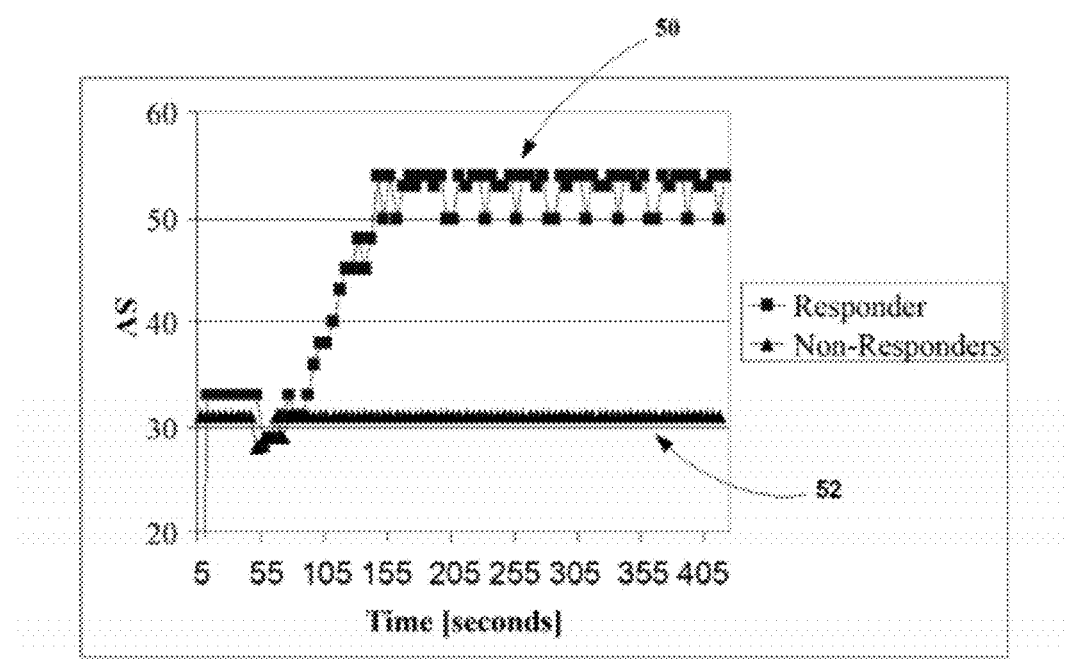
FIG. 4 is a plot comparing the simulate stroke volumes (SV) of a responder and a non-responder to CRT, as a function of time.

FIG. 4 shows simulated stroke volumes (SV) in milliliters (ml) of a responder and a non-responder to CRT are as a function of time. At initialization the adaptive CRT device discerns the intrinsic conductance intervals (PRV and PLV) of the patient. After a criterion for the convergence of PRV and PLV is met, an automatic switch to adaptive CRT mode occurs. In the adaptive CRT mode, the AV delay and VV interval are changed dynamically according to the information obtained from installed hemodynamic sensors. In the event the patient is a responder to CRT, the device will change the pacing intervals in order to achieve a higher stroke volume as depicted by data points 50. In the event the patient is a non-responder, the stroke volume will not increase and will remain unchanged as seen in data points 52. The responder curve visualizes a hemodynamic parameter as a function of time, and is presented on the graphical interface. Optionally, the responder curve demonstrates a stroke volume obtained beat after beat by implanted hemodynamic sensor 120 with dynamically optimized atrioventricular delay and interventricular interval parameters. Upon identification of a non-responder to hemodynamically derived automatic adjustment of pacing intervals, the identification of being a responder to CRT, or not being a responder to CRT, according to the presented responder curve, the clinician installing the CRT device may consider other options, including changing the position of the implanted leads in the right ventricle or the left ventricle and/or to select a configuration of the pacing leads with a multi-site lead in order to achieve an improved response to CRT at implantation. Stroke volume is one example of a hemodynamic performance target for optimization. Other hemodynamic performance targets may also be used with this invention such as a maximal ventricle pressure time derivative (max dp/dt), ejection fraction, cardiac output etc.

Another aspect of U.S. Pat. No. 7,657,313 and the present invention is an external adaptive CRT device to be used as an active diagnostic tool for identification of CRT responders, for finding optimal lead sites and optimal pacing intervals during CRT implantation for implanted or external adaptive and non-adaptive CRT devices as well. More specifically, current methods applied to achieve the best hemodynamic performance for a non-adaptive CRT device employ a programmer to select various combinations of different values of AV delay and VV interval and to identify the combination of particular AV delay value and VV interval value that yield the best hemodynamic performance. In accordance with embodiments of the present invention, an external adaptive closed-loop CRT programmer device is implemented, employing a learning module, which learns the best optimal AV delay and VV interval parameters and presents them to the clinician visually during CRT implantation. Thus, non-adaptive CRT devices may also benefit from the external adaptive CRT programmer device equipped with a learning module such as neural network module that is used at CRT implantation to identify CRT responders, to find the optimal pacing sites and pacing interval values and then program a non-adaptive CRT device with the best customable AV delay and VV interval parameters based on adaptive learning as opposed to blind scan of multiple AV delay and VV interval pairs that is still currently practiced. Obviously, the learning task may be executed during CRT implantation as well as at rest and exercise conditions in follow-up sessions, and thus several sets of AV delay and VV interval parameters may be formulated by such intelligent external close-loop programmer and substitute existing non learning external programming. This can be used as a supplementary tool for a CRT device programmer.

In accordance with the present invention, the PRV vs. PLV diagram at maximal stroke volumes represented in FIG. 2 can be presented on a clinician's graphical interface (typically a display device) to enable the clinician to make a decision as regards the optimal AV delay and VV interval to be programmed in the implanted CRT device. With both external and implanted adaptive CRT devices, if the response to the CRT is not satisfactory, the clinician is able to change the lead position and re-start the adaptive CRT device to repeatedly perform optimizations of the pacing interval until satisfactory results are obtained.

In addition to the active diagnostic benefit relating to implanted adaptive CRT devices explained above, which is typically implemented in a procedure room during device implantation, the use of the PRV vs. PLV diagonal diagram and the responder curve diagram is beneficial in other aspects. It simplifies patients' follow-up routines at hospitals and clinics. It can also be transmitted using an RF communication channel from the implanted device at the patient's home to a remote computer and hence to be used as a part of a remote telemedicine monitoring system. Such a monitoring system presents, according to this invention, the measured hemodynamic response to pacing with dynamically optimized AV delay and VV interval parameters heartbeat after heartbeat visually on an external programmer screen or on a remote computer screen.

With regard to implanted adaptive CRT devices, in addition to monitoring the hemodynamic response to pacing with dynamically optimized AV delay and VV interval parameters as explained above, the PRV vs. PLV diagram and responder curve diagram can be used to monitor pacing consistency and efficacy during various daily activities at rest and during exercise, and hence can provide information otherwise unavailable today. The calculated stroke volume extracted from the hemodynamic sensor and the PRV vs. PLV diagram are two examples of analysis and presentation of the hemodynamic response to pacing therapy with dynamically optimized AV delay and VV interval parameters delivered by the implanted adaptive CRT device. The present invention is not limited only to these presentations of the adaptive CRT device operation, and any other such presentations of hemodynamic response to pacing with dynamically optimized AV delay and VV interval parameters are included in this invention.

AV delay optimization of dual chamber pacemakers and defibrillators are as important clinically as the AV delay optimization of CRT devices. Dual chamber devices use one atrial electrode and one ventricular electrode, and ventricular pacing occurs after the pre-programmed AV delay measured from a sensed or paced atrial event ends. The AV delay depends on heart rate and on stress conditions and vary from patient to patient and during patient's daily activities; therefore a fixed pre-programmed AV delay is a less than optimal solution. Loss of AV delay synchrony is a major cause for pacemaker syndrome as quoted in Beyerbach D. M. and Cadman C. Oct. 10, 2002, in http://www.emedicine.com/med/topic2919.htm "Pacemaker Syndrome", the contents of which are incorporated herein by reference. Ellenbogen et al. (cited above) focused on clinical utility and proposed that "pacemaker syndrome represents the clinical consequences of AV dyssynchrony or sub-optimal AV synchrony, regardless of the pacing mode."

The present invention for optimizing and monitoring adaptive CRT (and CRT-D) devices is equally applicable to adaptive dual chamber devices with dynamic optimization of the AV delay only according to an implantable hemodynamic sensor and using a neural network processor in the same way as performed with adaptive CRT devices, described in U.S. Pat. No. 7,657,313.

It should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

What is claimed is:

1. A method for visualization and optimization of cardiac resynchronization therapy (CRT) for a patient, the method comprising:

implanting, during an implantation process, a pulse generator and associated leads in both a right ventricle of the patient and a left ventricle of the patient, said associated leads implanted in an initial position and an initial configuration;

communicating with an adaptive CRT device, said adaptive CRT device comprising a neural network module and an algorithmic module, said neural network module calculating a prediction of optimal pacing parameters and, responsive to control of said algorithmic module, said adaptive CRT device dynamically changing initial pacing parameters which define an initial right ventricular pacing interval (PRV) and an initial left ventricular pacing interval (PLV) to predicted optimal pacing parameters and said adaptive CRT device further applying said predicted optical pacing parameters to the patient via said implanted pulse generator during an electrophysiology study portion of the implantation process, the applied predicted optimal pacing parameters defining a predicted optimal PRV and a predicted optimal PLV;

presenting, during the electrophysiology study portion of the implantation process, a diagram of said applied predicted optimal PRV vs. said applied predicted optimal PLV on a graphical interface;

presenting, during the electrophysiology study portion of the implantation process, a responder curve on the graphical interface, wherein said responder curve displays a graph of a hemodynamic parameter performance of the patient as a function of time responsive to the dynamically applied predicted optimal pacing parameters;

when the displayed responder curve is indicative that the patient is a non-responder, defined as where the displayed responder curve does not indicate an increased hemodynamic parameter performance over time responsive to the dynamically applied predicted optimal pacing parameters, either:

a) changing the position, during the implantation process, from said initial position, of one of the implanted pacing lead in the right ventricle and the implanted pacing lead in the left ventricle of the patient; or b) changing a configuration of the implanted pacing leads, during the implantation process, from said initial configuration, of one of the right ventricle associated lead and the left ventricle associated lead to a multi-site lead, and when the displayed responder curve is indicative that the patient is a responder, defined as where the displayed responder curve indicates an increased hemodynamic parameter performance over time responsive to said applied predicted optimal pacing parameters of the adaptive CRT device, providing on-going pacing parameters to the patient via said implanted pulse generator and the associated leads at the implanted initial position and initial configuration responsive to the adaptive CRT device.

2. The method of claim 1, wherein the adaptive CRT device is part of the pulse generator.

3. The method of claim 1, further comprising a non-adaptive CRT device as the pulse generator, the predicted optimal pacing parameters being provided to the non-adaptive implanted CRT device by said adaptive CRT device.

4. A method for visualization and optimization of cardiac resynchronization therapy (CRT) for a patient, the method comprising:

implanting, during an implantation process, a pulse generator and associated leads in both a right ventricle of the patient and a left ventricle of the patient, said associated leads implanted in an initial position and an initial configuration;

communicating with an adaptive CRT device, said adaptive CRT device comprising a neural network module and an algorithmic module, said neural network module calculating a prediction of optimal pacing parameters and, responsive to control of said algorithmic module, dynamically changing initial pacing parameters to the predicted optimal pacing parameters and dynamically applying the predicted optimal pacing parameters to the patient via said implanted pulse generator during an electrophysiology study portion of the implantation process;

presenting, during the electrophysiology study portion of the implantation process, a responder curve on a graphical interface, wherein said responder curve displays a graph of a hemodynamic parameter performance of the patient as a function of time responsive to the dynamically applied predicted optimal pacing parameters;

when the displayed responder curve is indicative that the patient is a non-responder, defined as where the displayed responder curve does not indicate an increased hemodynamic parameter performance over time responsive to the dynamically applied predicted optimal pacing parameters provided by the adaptive CRT device, either:
a) changing the position, during the implantation process, from said initial position, of one of the implanted pacing lead in the right ventricle and the implanted pacing lead in the left ventricle of the patient; or
b) changing a configuration of the implanted pacing leads, during the implantation process, of one of the right ventricle associated lead and the left ventricle associated lead to a multi-site lead, when the displayed responder curve is indicative that the patient is a responder, defined as where the displayed responder curve indicates an increased hemodynamic parameter performance over time responsive to the adaptive CRT device, providing on-going pacing parameters to the patient via said implanted pulse generator and the associated leads at the implanted initial position and initial configuration responsive to the adaptive CRT device.

5. The method of claim 4, wherein the adaptive CRT device is part of the pulse generator.

6. The method of claim 4, further comprising a non-adaptive CRT device as the pulse generator, the predicted optimal pacing parameters being provided to the non-adaptive implanted CRT device by said adaptive CRT device.

\* \* \* \* \*